US006287656B1

(12) United States Patent
Turner et al.

(10) Patent No.: US 6,287,656 B1
(45) Date of Patent: *Sep. 11, 2001

(54) LOW MELT VISCOSITY AMORPHOUS COPOLYESTERS HAVING IMPROVED RESISTANCE TO LIPIDS

(75) Inventors: S. Richard Turner, Kingsport; Gary W. Connell, Church Hill; Bobby J. Sublett, Kingsport, all of TN (US)

(73) Assignee: Eastman Chemical Corporation, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/726,478

(22) Filed: Dec. 1, 2000

Related U.S. Application Data

(63) Continuation-in-part of application No. 09/453,922, filed on Apr. 28, 2000, now Pat. No. 6,183,848, which is a continuation-in-part of application No. 09/324,883, filed on Jun. 3, 1999, now Pat. No. 6,120,889.

(51) Int. Cl.$^7$ ............................. B29D 22/00; C08G 63/02
(52) U.S. Cl. ......................... 428/35.7; 528/97; 528/112; 528/176; 528/190; 528/219; 528/272; 528/294; 528/295; 528/302; 528/307; 528/308; 528/308.6; 428/221; 428/271; 428/357
(58) Field of Search ..................... 528/97, 112, 176, 528/190, 219, 272, 294, 295, 302, 307, 308, 308.6; 428/221, 271, 357, 35.7

(56) References Cited

U.S. PATENT DOCUMENTS

| | | | |
|---|---|---|---|
| 4,025,492 | 5/1977 | Binsack et al. | 260/75 R |
| 4,093,603 | 6/1978 | Jackson, Jr. et al. | 260/75 R |
| 4,136,089 | 1/1979 | Bier et al. | 528/309 |
| 4,176,224 | 11/1979 | Bier et al. | 528/309 |
| 4,188,357 | 2/1980 | Go | 264/540 |
| 4,208,527 | 6/1980 | Horlbeck et al. | 528/289 |
| 4,238,593 | 12/1980 | Duh | 528/272 |
| 4,307,060 | 12/1981 | Go | 264/540 |
| 4,547,563 | 10/1985 | Cholod | 528/173 |
| 5,183,863 | 2/1993 | Nakamura et al. | 525/438 |
| 5,191,057 | 3/1993 | Niki et al. | 528/190 |
| 5,235,024 | 8/1993 | Niki et al. | 528/190 |
| 5,356,989 | 10/1994 | Tachika et al. | 524/608 |
| 5,510,417 | 4/1996 | Tachika et al. | 524/608 |
| 5,519,066 | 5/1996 | McConnell et al. | 521/138 |
| 5,552,463 | 9/1996 | Akkapeddi et al. | 524/98 |
| 5,567,796 | 10/1996 | Nakatsukasa et al. | 528/272 |
| 5,599,858 | 2/1997 | Buchanan et al. | 524/41 |
| 5,663,238 | 9/1997 | Wang et al. | 525/285 |
| 5,681,918 | 10/1997 | Adams et al. | 528/279 |
| 5,731,401 | 3/1998 | Gupta et al. | 528/194 |

FOREIGN PATENT DOCUMENTS

| | | |
|---|---|---|
| 50-096692 | 7/1975 | (JP). |
| 4-173837 | 6/1992 | (JP). |
| 5-279464 | 10/1993 | (JP). |
| 8-283398 | 10/1996 | (JP). |
| 8-295731 | 11/1996 | (JP). |

OTHER PUBLICATIONS

Yang et al., "Physical Performance of Copolyesters for Medical Applications", *Journal of Applied Medical Polymers*, 3, No. 2, pp. 50–54, (Winter 1999) (copy enclosed).

*Primary Examiner*—Samuel A. Acquah
(74) *Attorney, Agent, or Firm*—Cheryl J. Tubach; Bernard J. Graves

(57) ABSTRACT

Amorphous copolyesters containing residues derived from 2,2'-[2,2-](sulfonylbis(4,1-phenyleneoxy))bis(ethanol). They exhibit enhanced heat distortion temperatures and glass transition temperatures without a significant increase in viscosity at low shear rates. The amorphous copolyesters also have improved resistance to attack by lipid solutions and are readily molded and extruded to form medial devices such as connectors, tubes, etc. which are useful for transport of lipids and other medical solutions.

20 Claims, No Drawings

US 6,287,656 B1

LOW MELT VISCOSITY AMORPHOUS COPOLYESTERS HAVING IMPROVED RESISTANCE TO LIPIDS

RELATED APPLICATIONS

This application is a continuation-in-part of U.S. application Ser. No. 09/453,922, filed Apr. 28, 2000 now U.S. Pat. No. 6,183,848 which in turn, is a continuation-in-part of U.S. application Ser. No. 09/324,883, filed Jun. 3, 1999, now U.S. Pat. No. 6,120,889, the disclosures of both applications being incorporated herein by reference in their entirety.

FIELD OF THE INVENTION

The invention relates to amorphous copolyesters containing 2,2'-(sulfonylbis(4,1-phenyleneoxy))bis(ethanol) or BDS. The amorphous copolyesters exhibit enhanced heat distortion temperatures and glass transition temperatures without a significant increase in viscosity at low shear rates. The amorphous copolyesters also have improved resistance to attack by lipid solutions and are readily molded and extruded to form shaped articles including medical devices such as connectors, tubes, etc. which are useful for transport of solutions containing lipid and other medical solutions.

BACKGROUND OF THE INVENTION

Amorphous copolyesters are generally defined as copolyesters that do not show a substantial melting point by differential scanning calorimetry when scanned at a rate of 20° C./min. These copolyesters are typically based on terephthalic acid, isophthalic acid, ethylene glycol, neopentyl glycol and 1,4-cyclohexanedimethanol. It is generally known in the art that amorphous copolyesters possess a combination of desirable properties, such as excellent clarity and color, toughness, chemical resistance and ease of processing. Accordingly, such copolyesters are known to be useful for the manufacture of extruded sheets, packaging materials, and shaped parts such as for medical devices. However, when compared to other families of materials such as polycarbonates based on bisphenol A and certain acrylic resins like polymethyl methacrylate, amorphous copolyesters generally have lower glass transition temperatures (Tg) and lower heat distortion temperatures (HDT). The lower Tg and HDT of amorphous polyesters inhibit their application where resistance to thermal deformation is important, for example, green house panels, skylights and other products prepared by extrusion or injection molding processes.

It is also important that amorphous copolyesters have a low shear melt viscosity. Unlike semi-crystalline polyesters, where ultimate molecular weight values can be raised by polymerization in the crystalline or solid state, high molecular weight amorphous copolyesters must be obtained directly in the melt phase polymerization. It is not possible or it is too expensive to render the amorphous copolyesters into a crystalline pellet or particle form. Further, when heated to the temperatures required for solid state polymerization, amorphous pellets or particles flow together and stick together.

As disclosed in the Journal of Applied Medical Polymers, Vol. 3, No. 2, pages 50–54 (Winter, 1999), polyethylene-co-1,4-cyclohexanedimethanol terephthalates (PETG and PCTG) are amorphous copolyesters which are useful in medical applications because of their transparent and colorless appearance and their flow properties that permit them to be molded into intricate medical connectors and devices. These copolyesters show excellent resistance to lipid solutions used in medical applications when there is no strain present. However when PETG and PCTG copolyesters are placed under strain, significant crazing and reduction in elongation to break values are observed.

Therefore, there is a need for shaped articles prepared from amorphous polyesters with high Tg and low, low shear melt viscosity that have improved resistance to lipid solutions at various levels of strain. The low melt viscosities at low shear rates are necessary for the amorphous polyester to flow through the reactor at a practical rate allowing the copolyesters to build to a useful molecular weight. It is known in the art that the molecular weight of copolyesters can be conveniently measured in terms of inherent viscosity ("IV"). Generally, an IV of 0.65 or higher is necessary for useful mechanical properties. Further, the maximum melt viscosity at 1 radian/second (shear rate) generally ranges from about 10,000 poise to about 12,000 poise at the temperature of the melt phase polymerization which is commonly in the range of about 260 to about 290° C.

Crystalline copolyesters with good heat resistance and high strength are disclosed by Japanese Patent No. 08295731. These copolyesters are based on terephthalic acid as the acid component and a mixture of 1,4-cyclohexanedimethanol, ethylene glycol, and ethylene oxide adducts of bisphenol as the glycol component. Amorphous copolyesters, however, are not disclosed.

A process for preparing polyesters with good transparency which are and useful in the production of bottles and films is disclosed by Japanese Patent No. 08283398. The process comprises the use of a specific antimony compound as a polycondensation catalyst. Polyester compositions for use in the preparation of optical instruments are disclosed by Japanese Patent No. 4173837. These copolyester compositions comprise an acid component consisting of terephthalic acid and a diol component consisting of 4,4'-bis(β-hydroxyethoxy)-diphenylsulfone (2,2'-(sulfonylbis-(4,1-phenyleneoxy))bis(ethanol)) and at least one aliphatic or alicyclic diol having from 2 to 12 carbon atoms and containing a specific combination of at least one metal and phosphorous. According to this Japanese patent, the specific combination of metal and phosphorous is necessary to obtain polyesters with sufficient transparency, hue, Tg, and heat resistance.

Japanese Patent No. 50096692 relates to a process for preparing polyesters from (A) a bifunctional carboxylic acid component composed primarily of terephthalic acid and/or an ester forming derivative thereof, (B) a diol with an aromatic nuclei composed primarily of 4,4'-bis-(β-hydroxyalkoxy)-diphenylsulfone (2,2'-(sulfonylbis-(4,1-phenyleneoxy))bis(ethanol)) and another diol. According to this Japanese patent, specific property limitations occur when a third diol, such as neopentyl glycol is incorporated.

Polyester sheets composed of ethylene glycol based glycols and terephthalic acid based dicarboxylic acids and containing diphenylsulfone and cyclohexane groups are disclosed by Japanese Patent No. 5279464. However, in order to obtain polyesters with superior transparency and heat resistant properties, the polyesters must contain both diphenylsulfone and cyclohexane groups at low levels.

U.S. Pat. No. 5,183,863 discloses viscoelastic resin compositions for vibration damping material. The resin comprises (A) at least one amorphous polyester resin of low specific gravity in which more than 40 mole % of the dibasic acid moiety is of aromatic type, (B) at least one amorphous polyester resin of high specific gravity in which more than 80 mole % of the dibasic acid is of aromatic type, and at least one hardener. As shown by Table 1 of the patent, the polyester resins according to this patent have relatively low Tg values ranging from −33 to 68° C.

U.S. Pat. Nos. 5,356,989 and 5,510,417 disclose aqueous dispersions suitable for use as coatings, paints, or adhesives which comprise a polyester resin, a water soluble organic compound, water, and a neutralizer. The polyester resins contain a polycarboxylic acid component and a polyol component. The glass transition temperature of the polyester resins according to these patents, however, range from −30° C. to 80° C.

Copolyesters randomly composed of a first repeating unit containing a naphthalene ring stricture and a second containing a naphthalene ring and an additional aryl ether linkage incorporated into the main chain are disclosed by U.S. Pat. No. 5,663,238. According to this patent, the copolyesters have improved solubility and are useful in various applications such as paints, varnishes, and structural adhesives. However, these properties can only be obtained with the specific combination of naphthalene and additional aryl ether linkage.

A copolyester of terephthalate and 2,2'-(sulfonylbis(4,1-phenyleneoxy))bis(ethanol) is disclosed in U.S. Pat. No. 4,547,563. However, the glass transition temperature of the copolyester is at most 85° C. and there is no teaching or suggestion that the incorporation of 2,2'-(sulfonylbis(4,1-phenyleneoxy))bis(ethanol) would improve the melt viscosity, glass transition temperature and resistance to lipids of amorphous copolyesters. Further, U.S. Pat. Nos. 4,188,357 and 4,307,060 disclose copolyesters of terephthalic acid, 2,2'-(sulfonylbis(4,1-phenyleneoxy))bis (ethanol), ethylene glycol and a trifunctional crosslinking agent, such as trimellitic acid. According to these patents, the trifunctional crosslinking agent is necessary to obtain copolyesters with effective melt strength non-Newtonian properties.

Accordingly, there remains a need for high IV and low melt viscosity amorphous copolyesters having sufficiently high glass transition temperatures and enhanced heat distortion temperatures yielding copolyesters which can be shaped into articles with enhanced chemical resistance, lipid resistance and mechanical properties, i.e., toughness, without requiring the specific parameters described above. The invention answers this need.

SUMMARY OF THE INVENTION

It has been discovered that when the diol component of an amorphous copolyester comprises residues of from about 5 to about 50 mole % of a 2,2'-(sulfonylbis (4,1-phenyleneoxy))-bis(ethanol), the melt viscosities and glass transition temperatures of such copolyesters are improved. Indeed, the invention relates to shaped articles such as medical devices prepared from an amorphous copolyester having a maximum melt viscosity at 1 radian/second and at about 260 to about 290° C. of about 12,000 poise; a glass transition temperature ranging from about 88° C. to about 120° C.; and an inherent viscosity of at least about 0.6. Such amorphous copolyesters comprise the reaction product of a diol component and a dicarboxylic acid component. The diol component comprises residues of from about 5 to about 50 mole % of 2,2'-(sulfonylbis (4,1-phenyleneoxy))-bis (ethanol) and from about 50 to about 95 mole % of a mixture of at least two diols selected from ethylene glycol, neopentyl glycol, 1,3-propanediol, 1,4-butanediol, 1,4-cyclohexanedimethanol, and mixtures thereof, wherein the total diol component is based on 100 mole %. The dicarboxylic acid component of the copolyesters according to the invention comprises residues of terephthalic acid, isophthalic acid, 1,4-cyclohexanedicarboxylic acid, 2,6-naphthalene dicarboxylic acid, and functional derivatives and mixtures thereof.

Because the copolyesters according to the invention surprisingly have relatively low melt viscosities at low shear rates, they can be readily prepared in conventional low-shear melt phase polyester manufacturing equipment. Further, due to the low melt viscosities, the IV or molecular weight of the copolyesters according to the invention is easily increased to yield copolyesters with useful mechanical properties, i.e., toughness. Because the melt viscosities are not high, the copolyesters of the invention can be molded using conventional techniques into small and intricate shaped articles such as medical parts for use in medical fluid transport, etc. The lipid resistance of the copolyesters under external strain makes them particularly useful in preparing shaped articles including medical devices such as tubes, pump housings, connectors, etc. where lipid resistance is important. In addition, because the copolyesters of the invention have relatively high glass transition temperatures and heat distortion temperatures, they withstand heat-aging sterilization procedures with ethylene oxide. The high glass transition temperature also permits extremely fast cycle times in injection molding processes for manufacturing medical parts and other devices. Accordingly, the invention also relates to molded and extruded articles, parts, devices, and films made from a copolyester as described above.

Additional objects and advantages of the invention are discussed in the detailed description which follows, and will be obvious from that description, or may be learned by practice of the invention. It is to be understood that both this summary and the following detailed description are exemplary and explanatory only and are not intended to restrict the invention in any way.

DETAILED DESCRIPTION OF THE INVENTION

The invention relates to an amorphous copolyester having a maximum melt viscosity at 1 radian/second (shear rate) and at about 260 to about 290° C. of about 12,000 poise; a glass transition temperature ranging from about 88° C. to about 120° C.; and an inherent viscosity of at least about 0.6. As part of its diol component, the amorphous copolyesters comprise residues of 2,2'-(sulfonylbis (4,1-phenyleneoxy)) bis(ethanol) ("BDS") which has the following chemical formula:

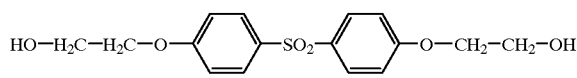

The presence of BDS provides the copolyester with enhanced glass transition temperatures and heat distortion temperatures while surprisingly maintaining the relatively low, low shear rate melt viscosities of commercial amorphous copolyesters. The amorphous copolyesters of the invention are the reaction product of a diol component and a dicarboxylic acid component, as described below.

The diol component comprises residues of from about 5 to about 50 mole %, more preferably from about 10 to about 50 mole %, of BDS and about 50 to 95 mole %, more preferably from about 50 to about 90 mole %, of a mixture of at least two diols selected from the group consisting of ethylene glycol, neopentyl glycol, 1,3-propanediol, 1,4- butanediol, 1,4-cyclohexanedimethanol, and mixtures thereof. In a preferred embodiment, the diol component comprises residues of from about 10 to about 50 mole % BDS and from about 50 to about 90 mole % of a mixture at least two diols selected from the group consisting of ethylene glycol, neopentyl glycol, cyclohexanedimethanol, and mixtures thereof. While the mole ratio of the diols in the mixture of at least two diols may vary as long as the desired properties discussed above are achieved, the minimum amount of any particular diol should be at least 1 mole %.

The mole % of each diol, including BDS and the diols from the mixture of at least two diols in the diol component adds up to a total of 100 mole %. For example, when the diol component contains BDS and a mixture of two other diols (as discussed above), the diol component of the amorphous copolyester of the invention can easily be represented by the following formula:

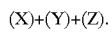

(X)+(Y)+(Z).

In the formula, X is the mole % of BDS which ranges from 5 to 50, as discussed above. Where the mixture of at least two diols in the amorphous copolyester contains only two diols, Y and Z represent the mole % of the two diols and range from 50 to 95 mole %. In such a preferred embodiment, the mole ratio of Y to Z may vary widely as long as an amorphous copolyester with the desired properties is achieved. Generally, for example, the mole ratio of Y to Z ranges from 1:94 to 1:1. For example, as illustrated by the examples below, the mole ratio of Y to Z can range from 1:2, 1:3, 1:4, 1:6, and 1:7. In embodiments where the mixture of at least two diols is a mixture of three or more diols, similar ranges of mole ratios may be used.

The dicarboxylic acid component comprises residues of terephthalic acid, isophthalic acid, 1,4-cyclohexanedicarboxylic acid, 2,6-naphthalenedicarboxylic acid, or mixtures thereof. Also suitable are the anhydrides thereof, acid chlorides thereof, and lower, e.g., $C_1$–$C_8$ alkyl esters thereof. Any isomers of the dicarboxylic acid component or mixtures thereof may be used. For example, cis, trans, or cis/trans mixtures of 1,4-cyclohexanedicarboxylic acid may be employed. Examples of suitable naphthalenedicarboxylic acid isomers include 1,4-naphthalenedicarboxylic acid, 2-6-naphthalenedicarboxylic acid, 2,7-naphthalenedicarboxylic acid or mixtures thereof. Preferably, the dicarboxylic acid component is terephthalic acid.

As discussed above, the amorphous copolyesters according to the invention have enhanced glass transition and heat distortion temperatures and exhibit improved resistance to thermal deformation in applications where heat is generated. In this regard, the glass transition temperature of the copolyesters of the invention range from about 88° C. to about 120° C., more preferably from about 90 to about 110° C., as determined by Differential Scanning Calorimetry (DSC) at a heating rate of 20° C./min, generally to a temperature of 280–300° C., in a nitrogen atmosphere.

Further, amorphous copolyesters according to the invention have a maximum melt viscosity at 1 radian/second (shear rate) and at about 260 to about 290° C. of about 15,000 poise as determined by a temperature drop experiment from 290 to 120° C. with a 10 degree interval on a Rheometrics Dynamic Analyzer (RDA II) with 25 mm diameter parallel plates. In a preferred embodiment, the amorphous copolyester of the invention has a melt viscosity ranging from about 3000 poise to about 11,000 poise, most preferably from about 4000 to about 10,000 poise.

As discussed above, the presence of BDS in the copolyester of the invention significantly increases the glass transition temperature and the heat distortion temperature. Further, it has surprisingly been discovered that the low shear rate melt viscosity of the copolyesters of the invention is not increased over that of lower glass transition temperature commercial amorphous copolyesters that do not contain BDS. Due to the low melt viscosity of the copolyester of the invention, its molecular weight (measured as IV) is advantageously increased yielding copolyesters with enhanced mechanical properties, i.e., toughness. Generally, the copolyesters of the invention have an IV of at least about 0.6 measured at a temperature of 25° C. at 0.25 g/dl concentration in a solvent mixture of symmetric tetrachloroethane and phenol having a weight ratio of symmetric tetrachloroethane to phenol of 2:3. In a preferred embodiment, the IV ranges from about 0.65 to about 0.90 dl/g, more preferably, from about 0.70 to about 0.80.

The amorphous copolyesters according to the invention are prepared by conventional polymerization processes known in the art, such as disclosed by U.S. Pat. Nos. 4,093,603 and 5,681,918, the disclosures of which are herein incorporated by reference. Examples of polycondensation processes useful in the present invention include melt phase processes conducted with the introduction of an inert gas stream, such as nitrogen, to shift the equilibrium and advance to high molecular weight or the more conventional vacuum melt phase polycondensations, at temperatures ranging from about 240° C. to about 300° C. or higher which are practiced commercially. Although not required, conventional additives may be added to the copolyesters of the invention in typical amounts. Such additives include pigments, colorants, stabilizers, antioxidants, extrusion aids, slip agents, carbon black, flame retardants and mixtures thereof.

Typical preparations of the amorphous copolyesters of the invention are shown in the examples below.

As discussed, it may be preferable to conduct the polymerization reaction in the presence of one or more conventional polymerization catalysts. Typical catalysts or catalyst systems for polyester condensation are well-known in the art. Suitable catalysts are disclosed, for example, in U.S. Pat. Nos. 4,025,492, 4,136,089, 4,176,224, 4,238,593, and 4,208,527, the disclosures of which are herein incorporated by reference. Further, R. E. Wilfong, Journal of Polymer Science, 54, 385 (1961), the disclosure of which is herein incorporated by reference, describes typical catalysts which are useful in polyester condensation reactions. Preferred catalyst systems include Mn/Ti/Co/P, Mn/Ti/P, Zn/Ti/Co/P, Zn/Al. When cobalt is not used in the polycondensation, the use of polymerizable toners are required to control the color of these amorphous copolyesters so that they are suitable for the intended applications where color may be an important property. In addition to the catalysts and toners, other additives, such as antioxidants, dyes, etc. may be used in the copolyesterifications.

Due to the relatively high glass transition temperature and heat distortion temperature of the copolyesters according to the invention, the copolyesters are extremely useful for applications in extruded heavy gauge sheet, extruded film and other plastic applications. Common plastic processing techniques such as compression molding, injection molding, and extrusion can be successfully used to manufacture useful articles from these copolyesters. Accordingly, another embodiment of the invention relates to shaped articles, sheets, and films having improved resistance to lipid solutions prepared from the copolyester compositions described above. Depending on the catalyst system used and the polycondensation process conditions, the shaped articles, sheets, and films according to the invention can be transparent, preferably having an L* color value of at least about 70, an a* value ranging from about (–)1.5 to 1.5 and a b* value ranging from about (–)1.5 to 1.5.

Generally, a copolyester of the invention is shaped into an unoriented, low crystallinity, transparent sheet by drying the resin, extruding the resulting resin into a sheet using, for example, inflation or pressing techniques or an extruder fitted with an appropriately configured sheet-forming die, for example, a T-die extruder. Preferably, the sheet has a thickness ranging from about 5 mil to about 40 mil. The sheet is then contacted with a casting drum, such as chill roll, set at a sufficiently low temperature to thereby quench and solidify the sheet. The resulting sheet may then be thermally formed into a container having a desired shape by conventional thermoforming processes known in the art, including but not limited to, vacuum forming and pressure forming processes.

In another embodiment, the quenched sheet may be oriented minimally either monoaxially or biaxially by techniques known in the art. For biaxial extension, for example, the longitudinal and lateral extensions may be conducted at a temperature ranging from about 60° C. to about 150° C. in a draw ratio of about 2.5 to about 6.0 using, for example, a T. M. Long stretching apparatus. Preferably, the draw ratio in both longitudinal and lateral directions ranges from about 2.5 to about 4.0. A biaxially extended film according to the invention generally has a thickness ranging from about 0.2 mil to about 2.5 mil, more preferably from about 0.5 mil to about 1.0 mil.

Sheeting made from clear, colored, or pigmented copolyesters of this invention can be advantageously employed in a great number of applications where the enhanced resistance to thermal deformation or flow provided by these copolyesters is important. Such examples include, but are not limited to skylights, solar roof panels, sign boards, greenhouse panels, marquees on stores, etc. The copolyesters of the invention may be used as a single sheet or as coextruded sheets in these kinds of applications with UV protection or color layers contiguous to the enhanced Tg copolyester layer. The higher heat distortion temperatures of the amorphous copolyesters of the invention are also useful in medical areas where articles with improved sterilization performance and improved chemical resistance are desired.

Shaped articles manufactured from the copolyesters of this invention have unexpected improvement in resistance to attack by medical lipid solutions. This is manifested by retention of elongation to break values (retention of toughness) and significant reduction of visual crazing in molded test bars and medical parts, such as connectors, devices, tubing, etc.

EXAMPLES

The following examples are intended to illustrate, but not limit, the scope of the present invention. The inherent viscosities were measured at a temperature of 25° C. at 0.25 g/dl concentration in a solvent mixture of symmetric tetrachloroethane and phenol having a weight ratio of symmetric tetrachloroethane to phenol of 2:3. The $2^{nd}$ cycle glass transition temperatures were determined according to DSC at a heating rate of 20° C./min to a temperature of 280–300° C., quenching in liquid nitrogen to 0° C., and then rerunning the sample and recording the Tg as the $2^{nd}$ cycle glass transition temperature. The melt viscosities were determined by a temperature drop experiment from 290 to 220° C. with a 10 degree interval on a Rheometrics Dynamic Analyzer (RDA II) with 25 mm diameter parallel plates. Final copolyester compositions were determined by proton NMR analysis on a 600 MHz JEOL instrument. The oxygen permeability rate of the compression molded non-oriented films was determined using ASTM standard D3985.

Example 1

A copolyester based on terephthalic acid with a diol composition of 23.3% neopentyl glycol, 61% 1,4-cyclohexanedimethanol, and 15.7% of BDS was prepared as follows. To a 500 ml round bottom flask equipped with a ground glass head, a stirrer and a nitrogen inlet was added 77.6 grams (0.40 moles) of dimethyl terephthalate, 13.1 grams (0.13 moles) of neopentyl glycol, 36.1 grams (0.25 moles) of 1,4-cyclohexanedimethanol, and 21.3 grams (0.06 moles) of BDS. Enough titanium catalyst was added to give 100 parts per million (ppm) titanium in the polymer. The flask was immersed into a Belmont metal bath and heated for 1.5 hr at 200° C. and 2 hr at 210° C. After this time the theoretical amount of methanol was collected and the temperature was increased to 275° C. The pressure in the flask was reduced from atmospheric to between 0.1 and 0.5 mm of Hg over 5 minutes. The temperature was maintained at 275° C. and the pressure between 0.1 to 0.5 mm for 30 minutes. Stirring was reduced as viscosity increased until a minimum stir rate of 15 RPM was obtained. The vacuum was discontinued and nitrogen bled into the flask. The polymer was allowed to cool, removed from the flask, and ground to pass a 3 mm screen. The resulting copolyester had an inherent viscosity of 0.73 dL/g and a $2^{nd}$ cycle glass transition temperature of 100.3° C. The melt viscosity for this copolyester for 1 rad/sec at 280° C. was 5724. The color values were as follows: L*=83.41; a*=(–) 1.17, b*=3.53.

Example 2

A copolyester based on terephthalic acid with a diol composition of 17.5% ethylene glycol, 72.9% 1,4-cyclohexanedimethanol, and 9.6% BDS was prepared as follows. To a 500 ml round bottom flask equipped with a ground glass head, a stirrer and a nitrogen inlet was added 77.6 grams (0.40 moles) of dimethyl terephthalate, 25.1 grams (0.40 moles) of ethylene glycol, 51.3 grams (0.36 moles) of 1,4-cyclohexanedimethanol, and 13.5 grams (0.04 moles) of BDS. Enough titanium, manganese, and cobalt catalyst was added to give 60, 55, and 75 parts per million (ppm) respectively in the polymer. The flask was immersed into a Belmont metal bath and heated for 1.5 hr at 200° C. and 2 hr at 210° C. After this time the theoretical amount of methanol was collected. Enough phosphorous was added to give 85 ppm in the polymer and the temperature was increased to 280° C. The pressure in the flask was reduced from atmospheric to between 0.1 and 0.5 mm of Hg over 5 minutes. The temperature was maintained at 280° C. and the pressure between 0.1 to 0.5 mm for 30 minutes. Stirring was reduced as viscosity increased until a minimum stir rate of 15 RPM was obtained. The vacuum was discontinued and nitrogen bled into the flask. The polymer was allowed to cool, removed from the flask, and ground to pass a 3 mm screen. The resulting copolyester had an inherent viscosity of 0.77 dL/g and a $2^{nd}$ cycle glass transition temperature of 98.6° C. The melt viscosity of this copolyester for 1 rad/sec at 280° C. was 10,305.

Example 3

A copolyester based on terephthalic acid with a diol composition of 56.4% ethylene glycol, 28.3% 1,4-cyclohexanedimethanol, and 15.3% BDS was prepared as follows. To a 500 ml round bottom flask equipped with a ground glass head, a stirrer and a nitrogen inlet was added 97.8 grams (0.50 moles) of dimethyl terephthalate, 47.6 grams (0.77 moles) of ethylene glycol, 23.3 grams (0.16 moles) of 1,4-cyclohexanedimethanol, and 26.6 grams (0.08 moles) of BDS. Enough titanium and manganese catalysts were added to give 16 parts per million (ppm) titanium and 46 ppm manganese in the polymer. Red and blue toners were added to give 2 ppm red dye and 3 ppm blue dye in the final polymer. The flask was immersed into a Belmont metal bath and heated for 1.5 hr at 200° C. and 2 hr at 210° C. After this time the theoretical amount of methanol was collected. Enough phosphorous catalyst was added to give 75 ppm in the polymer and the temperature was increased to 285° C. The pressure in the flask was reduced from atmospheric to 0.5 mm of Hg over 5 minutes. The temperature was maintained at 285° C. and the pressure at 0.5 mm for 30 minutes. Stirring was reduced as viscosity increased until a minimum stir rate of 15 RPM was obtained. The pressure in the flask was reduced from 0.5 to 0.4 mm of Hg over 1 minute. The temperature was maintained at 285° C. and the pressure at 0.4 mm for 100 minutes. The vacuum was discontinued and nitrogen bled into the flask. The polymer was allowed to cool, removed from the flask, and ground to pass a 3 mm screen. The resulting copolyester had an inherent viscosity of 0.71 dL/g and a $2^{nd}$ cycle glass transition temperature of 97.7° C. The color values were as follows: L*=78.44, a*=0.48, b*=(−)0.92. The melt viscosity at 290° C., 280° C., 270° C., and 260° C. was 4784, 5460, 6520, and 7842 poise respectively.

Example 4

A copolyester based on terephthalic acid with a diol composition of 55.9% ethylene glycol, 28.9% 1,4-cyclohexanedimethanol, and 15.2% BDS was prepared as follows. To a 500 ml round bottom flask equipped with a ground glass head, a stirrer and a nitrogen inlet was added 97.0 grams (0.50 moles) of dimethyl terephthalate, 47.6 grams (0.77 moles) of ethylene glycol, 23.3 grams (0.16 moles) of 1,4-cyclohexanedimethanol, and 26.6 grams (0.08 moles) of BDS. Enough titanium and manganese catalysts were added to give 16 parts per million (ppm) titanium and 46 ppm manganese in the polymer. The flask was immersed into a Belmont metal bath and heated for 1.5 hr at 200° C. and 2 hr at 210° C. After this time the theoretical amount of methanol was collected. Enough phosphorous catalyst was added to give 75 ppm in the polymer and the temperature was increased to 285° C. The pressure in the flask was reduced from atmospheric to 0.5 mm of Hg over 5 minutes. The temperature was maintained at 285° C. and the pressure at 0.5 mm for 30 minutes. Stirring was reduced as viscosity increased until a minimum stir rate of 15 RPM was obtained. The pressure in the flask was reduced from 0.5 to 0.4 mm of Hg over 1 minute. The temperature was maintained at 285° C. and the pressure at 0.4 mm for 100 minutes. The vacuum was discontinued and nitrogen bled into the flask. The polymer was allowed to cool, removed from the flask, and ground to pass a 3 mm screen. The resulting copolyester had an inherent viscosity of 0.71 dL/g and a $2^{nd}$ cycle glass transition temperature of 96.4° C. The melt viscosity for this copolyester for 1 rad/sec at 280° C. was 5464. The color values were as follows: L*=84.11, a*=(−) 1.49, b*=4.82.

Example 5

A copolyester based on terephthalic acid with a diol composition of 69.7% ethylene glycol, 10.8% 1,4-cyclohexanedimethanol, and 19.5% BDS was prepared as follows. To a 500 ml round bottom flask equipped with a ground glass head, a stirrer, and a nitrogen inlet was added 97.0 grams (0.50 moles) of dimethylterephthalate, 42.8 grams (0.69 moles) of ethylene glycol, 7.9 grams (0.055 moles) of 1,4-cyclohexanedimethanol, and 33.8 grams (0.10 moles) of BDS. Enough titanium, manganese and cobalt catalyst was added to give 60, 55, and 75 parts per million (ppm), respectively in the polymer. The flask was immersed in a Belmont metal bath and was heated for 1.5 hours at 200° C. and 2 hours at 210° C. After this time the theoretical amount of methanol had been collected. Enough phosphorus catalyst was added to give 85 ppm in the polymer and the temperature increased to 280° C. The pressure in the flask was reduced from atmospheric to between 0.1 to 0.5 mm of Hg over 5 minutes. The temperature was maintained at 280° C. and the pressure between 0.1 to 0.5 mm for 30 minutes. Stirring was reduced as viscosity increased until a minimum stir rate of 15 RPM was obtained. The vacuum was discontinued and nitrogen bled into the flask. The polymer was allowed to cool, removed from the flask and ground to pass a 3-mm screen. The inherent viscosity of the polymer was 0.706 dL/g and $2^{nd}$ cycle glass transition temperature of 98° C. as determined by DSC. The heat distortion temperature was measured according to ASTM-D648 at 264 psi as 77° C. The heat distortion temperature is defined in ASTM-D648 as the temperature at a stress of 264 psi where an F-1 molded bar deflects 0.01 inches when heated in an oil bath at 2° C./min.

Comparative Example 6

A copolyester based on terephthalic acid with a diol composition of 40% ethylene glycol, 40% 1,4-cyclohexanedimethanol and 20% 2,2,4,4-tetramethyl-1,3-cyclobutanediol was prepared by adding 77.6 g (0.40 moles) dimethyl terephthalate, 32.3 g (0.52 moles) ethylene glycol, 24.4 g (0.17 moles) 1,4-cyclohexaniedimethanol, and 15.8 g (0.11 moles) of 2,2,4,4-tetramethyl-1,3-cyclobutanediol to a 500 ml glass round bottom polymerization reactor equipped with a stirrer and nitrogen inlet. To this mixture was added 1.09 milliliters of a solution containing 13.5 g of dibutyltin diacetate in 50 ml of n-butanol. The flask was immersed into a Belmont metal bath and heated for 40 minutes at 200° C., 25 minutes at 215° C., and 160 minutes at 220° C. The theoretical amount of methanol was collected during this time. The temperature was increased to 285° C. and the pressure in the flask was reduced from atmospheric to between 0.1 and 0.5 mm Hg over 5 minutes. The temperature was maintained at 285° C. at this pressure for 20 minutes. Stirring was reduced as the melt viscosity increased until a minimum stir rate of 15 RPM was obtained. The vacuum was discontinued and nitrogen purged into the reactor. The polymer was cooled, removed from the flask and ground to pass a 3 mm screen. The inherent viscosity of the polymer was 0.72. The polymer had a $2^{nd}$ cycle glass transition temperature of 98° C. The melt viscosity at 1 radian per second at 280° C. was 33,000 poise.

Comparative Example 7

A copolyester was prepared as in Example 6 with a diol composition of 20% ethylene glycol, 55% 1,4-cyclohexanedimethanol, and 25% 2,2,4,4-tetramethylcyclobutane-1,3-diol. The resulting copolyester exhibited an IV of 0.79, had a $2^{nd}$ cycle glass transition temperature of 101° C., and a melt viscosity at 280° C. of 54,210 poise.

Example 8

This example demonstrates the effect inherent viscosity has on elongation to break. Elongation to break values greater than 100% signify excellent toughness in the plastic, while values less than 20% represent plastics with brittle behavior. The test used was ASTM D638 and was performed on injection molded Type 1 test bars using a constant strain rate of 0.1/in using a standard Instron Universal Tester. The results are set forth below in Table 1.

TABLE 1

| Diol Component | IV | Elongation to Break |
|---|---|---|
| 69% EG[1], 20% BDS, 11% CHDM[2] | 0.64 | 8% |
| 69% EG, 20% BDS, 11% CHDM | 0.71 | 189% |
| 69% EG, 31% CHDM | 0.72 | 267% |

[1]EG = ethylene glycol
[2]CHDM = 1,4-cyclohexanedimethanol

Example 9

In this Example, the resistance of amorphous polyesters to attack by lipid solutions was evaluated. Samples of PETG 6763 (a commercially available amorphous polyester derived from TPA and a glycol mixture of about 69 mol % EG and 31 mol % CHDM) and PCTG DN 004 (a commercially available amorphous polyester of TPA and a glycol mixture of about 62 mol % CHDM and about 38 mol % EG) were compared with samples of amorphous polyesters representative of this invention. Copolyester A was derived from terephthalic acid (TPA) and a glycol mixture of 69 mol % EG, 20 mol % BDS and 11 mol % CHDM and Copolyester B was derived from TPA and a glycol blend of 64 mol % CHDM, 16 mol % BDS and 20 mol % EG. Samples were injection molded into standard tensile test samples (ASTM-D638). The samples were exposed to Liposyn II 20% intravenous fat emulsion (lipid solution) for 72 hours at fixed strains of 0, 0.5, 1.5 and 2.7% by placing the bars on three-point-bend strain rigs. Exposure to the lipid solution was accomplished by placing a 1"x0.5" patch of filter paper over the center of the bar and saturating the patch with the lipid solution initially and then rewetting several times a day. The results of these tests are shown in Tables 2 and 3. Table 2 compares the results for Copolyester A vs. commercial PETG 6763 and Table 3 compares the results for Copolyester B vs. commercial PCTG DN004. The control represents samples prior to contact with lipid solution.

TABLE 2

| Material | Condition Strain (%) | Yield Strain (%) | Break Strain (%) | Yield Stress (MPa) | Break Stress (MPa) | Appearance |
|---|---|---|---|---|---|---|
| PETG 6763 | Control | 5.7 | 181.4 | 50.1 | 27.1 | A |
|  | 0.0 | 5.7 | 93.5 | 49.6 | 25.9 | A |
|  | 0.50 | 5.7 | 147.8 | 49.4 | 28.6 | A |
|  | 1.50 | 5.7 | 238.5 | 49.4 | 34.0 | C |
|  | 2.70 | 5.9 | 115.7 | 48.1 | 25.9 | C |
| Copolyester A | Control | 6.1 | 349.7 | 58.9 | 48.3 | A |
|  | 0.0 | 6.1 | 264.2 | 57.5 | 41.5 | A |
|  | 0.50 | 6.1 | 374.4 | 57.8 | 48.1 | A |
|  | 1.50 | 6.2 | 286.9 | 57.9 | 43.0 | A |
|  | 2.70 | 6.3 | 347.2 | 57.5 | 47.8 | C |

A - No effect; B - Discoloration; C - Edge crazes; D - Full width crazes

TABLE 3

| Material | Strain (%) | Yield Strain (%) | Break Strain (%) | Yield Stress (MPa) | Break Stress (MPa) | Appearance |
|---|---|---|---|---|---|---|
| Copolyester B | Control | 5.5 | 237.2 | 48.8 | 49.8 | A |
|  | 0.50 | 5.4 | 226.2 | 49.1 | 47.2 | A |
|  | 1.50 | 5.5 | 246.2 | 49.5 | 42.8 | A |
|  | 2.70 | 5.6 | 233.7 | 48.9 | 31.8 | A, C● |
| DN004 | Control | 4.7 | 285.0 | 43.4 | 40.7 | A |
|  | 0.50 | 4.9 | 289.5 | 46.7 | 43.8 | A |
|  | 1.50 | 4.9 | 296.0 | 46.8 | 43.3 | A |
|  | 2.70 | — | 6.9 | — | 29.5 | D |

A - No effect; B - Discoloration; C - Edge crazes; D - Full width crazes
●Some Examples exhibited minor edge crazing.

Inspection of the results in Tables 2 and 3 shows that the presence of BDS in the glycol mixture significantly enhanced the copolyesters' resistance to lipid solutions when the test samples were placed under high strain levels. For example, samples of copolyester PETG 6763 which contain no BDS, exhibited edge crazing at strain levels of 1.50% and 2.70% and suffered substantial reduction in elongation to break at a strain level of 2.70%. On the other hand, samples of Copolyester A in which 20 mol % of CHDM was replaced by BDS, showed no crazing at a strain level of 1.50% and no significant reduction in elongation to break at a strain level as high as 2.70%. Similar results are evident from the data in Table 3. Samples of Copolyester DN004 containing no BDS, showed substantial crazing and substantial reduction in elongation to break at a 2.70% strain level. In comparison, samples of Copolyester B at a strain level of 2.70% showed no significant reduction in elongation to break. Some samples at the 2.70% strain level showed no crazing while some showed slight edge crazing.

What is claimed is:

1. A medical device having improved resistance to lipids, said device prepared from an amorphous copolyester, wherein the amorphous copolyester is the reaction product of a diol component and a dicarboxylic acid component, wherein the diol component comprises residues of from about 5 to about 50 mole % of 2,2'-(sulfonylbis(4,1-phenyleneoxy))-bis(ethanol) and from about 50 to about 95 mole % of a mixture of at least two diols selected from the group consisting of ethylene glycol, neopentyl glycol, 1,3-propanediol, 1,4-butanediol, 1,4-cyclohexanedimethanol, and mixtures thereof; and the dicarboxylic acid component comprises residues of at least one compound selected from group consisting of terephthalic acid, isophthalic acid, 1,4-cyclohexandedicarboxylic acid, 2,6-naphthalene dicarboxylic acid, anhydrides thereof, acid chlorides thereof, lower alkyl esters thereof, and mixtures thereof.

2. The device according to claim 1, wherein the 2,2'-(sulfonylbis(4,1-phenyleneoxy))bis(ethanol) is present at from about 10 to about 50 mole %.

3. The device according to claim 1, wherein the mixture of at least two diols comprises ethylene glycol, neopentyl glycol and 1,4-cyclohexanedimethanol.

4. The device according to claim 1, wherein the diol component comprises residues of from about 10 to about 50 mole % of 2,2'-(sulfonylbis(4,1-phenyleneoxy))-bis(ethanol); and from about 50 to about 90 mole % of at least two diols selected from the group consisting of ethylene glycol, neopentyl glycol, 1,4-cyclohexanedimethanol, and mixtures thereof.

5. The device according to claim 1, wherein the dicarboxylic acid component comprises residues of terephthalic acid.

6. The device according to claim 1, wherein the amorphous copolyester has an inherent viscosity of at least about 0.6.

7. The device according to claim 6, wherein the amorphous copolyester has an inherent viscosity ranging from about 0.65 to about 0.9.

8. The device according to claim 7, wherein the amorphous copolyester has an inherent viscosity ranging from about 0.70 to about 0.80.

9. The device according to claim 1, wherein the amorphous copolyester has a maximum melt viscosity at 1 radian/second and about 260° C. to about 290° C. of about 15,000 poise.

10. The device according to claim 9, wherein the amorphous copolyester has a melt viscosity ranging from about 3000 poise to about 11,000 poise.

11. The device according to claim 1, wherein the amorphous copolyester has a glass transition temperature ranging from about 88° C. to about 120° C.

12. The device according to claim 1, wherein the amorphous copolyester has a glass transition temperature ranging from about 90° C. to about 110° C.

13. The device according to claim 1, which is transparent.

14. A medical device according to claim 1 in the shape of a tube.

15. A medical device according to claim 1 in the shape of a connector.

16. A medical device according to claim 1 in the shape of a pump housing.

17. A medical article for contacting solutions containing lipids, said article prepared from an amorphous copolyester comprising the reaction product of a diol component and a dicarboxylic acid component, wherein the diol component comprises residues of from about 5 to about 50 mole % of 2,2'-(sulfonylbis (4,1-phenyleneoxy))-bis(ethanol) and from about 50 to about 95 mole % of a mixture of at least two diols selected from the group consisting of ethylene glycol, neopentyl glycol, 1,3-propanediol, 1,4-butanediol, 1,4-cyclohexanedimethanol, and mixtures thereof; and the dicarboxylic acid component comprises residues of at least one compound selected from group consisting of terephthalic acid, isophthalic acid, 1,4-cyclohexandedicarboxylic acid, 2,6-naphthalene dicarboxylic acid, anhydrides thereof, acid chlorides thereof, lower alkyl esters thereof, and mixtures thereof.

18. An article according to claim 17 in the form of a medical device.

19. An article according to claim 18, wherein the medical device is a tube, connector or pump housing.

20. A shaped article having improved resistance to lipids, said article prepared from an amorphous copolyester comprising the reaction product of a diol component and a dicarboxylic acid component, wherein the diol component comprises residues of from about 5 to about 50 mole % of 2,2'-(sulfonylbis(4,1-phenyleneoxy))-bis(ethanol) and from about 50 to about 95 mole % of a mixture of at least two diols selected from the group consisting of ethylene glycol, neopentyl glycol, 1,3-propanediol, 1,4-butanediol, 1,4-cyclohexanedimethanol, and mixtures thereof; and the dicarboxylic acid component comprises residues of at least one compound selected from group consisting of terephthalic acid, isophthalic acid, 1,4-cyclohexandedicarboxylic acid, 2,6-naphthalene dicarboxylic acid, anhydrides thereof, acid chlorides thereof, lower alkyl esters thereof, and mixtures thereof.

* * * * *

UNITED STATES PATENT AND TRADEMARK OFFICE
CERTIFICATE OF CORRECTION

PATENT NO. : 6,287,656 B1
DATED : September 11, 2001
INVENTOR(S) : S. Richard Turner et al.

It is certified that error appears in the above-identified patent and that said Letters Patent is hereby corrected as shown below:

<u>Title page,</u>
Item [73], Assignee, delete "Corporation" and insert -- Company --;
Item [57], ABSTRACT,
Line 7, delete "medial" and insert -- medical --.

Signed and Sealed this

Twenty-fourth Day of September, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,287,656 B1
DATED : September 11, 2001
INVENTOR(S) : S. Richard Turner et al.

It is certified that error appears in the above-identified patent and that said Letters Patent is hereby corrected as shown below:

<u>Title page,</u>
Item [73], Assignee, delete "Corporation" and insert -- Company --;
Item [57], ABSTRACT,
Line 7, delete "medial" and insert -- medical --.

Signed and Sealed this

Fifteenth Day of October, 2002

*Attest:*

JAMES E. ROGAN
*Attesting Officer*    *Director of the United States Patent and Trademark Office*